(12) United States Patent
OHaRa

(10) Patent No.: US 7,883,859 B2
(45) Date of Patent: *Feb. 8, 2011

(54) METHOD FOR PRODUCING ACTIVE AND STABLE ACETYLCHOLINESTERASE BIOASSAY ELEMENT

(75) Inventor: Reiko OHaRa, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 311 days.

This patent is subject to a terminal disclaimer.

(21) Appl. No.: 11/637,825

(22) Filed: Dec. 13, 2006

(65) Prior Publication Data

US 2007/0148719 A1     Jun. 28, 2007

(30) Foreign Application Priority Data

Dec. 23, 2005  (TW) .............................. 94146157 A

(51) Int. Cl.
*G01N 33/543* (2006.01)
*C12M 3/00* (2006.01)

(52) U.S. Cl. ..................... 435/7.92; 435/20; 435/287.2; 435/177; 435/176; 435/180

(58) Field of Classification Search ...................... None
See application file for complete search history.

(56) References Cited

U.S. PATENT DOCUMENTS

| 4,749,487 | A | * | 6/1988 | Lefebvre | ..................... 210/490 |
| 5,413,804 | A | * | 5/1995 | Rhodes | ........................ 426/583 |
| 5,624,831 | A | * | 4/1997 | Vu Khue et al. | ............. 435/177 |
| 6,652,875 | B1 | * | 11/2003 | Bannister | .................... 424/440 |

OTHER PUBLICATIONS

Ellman et al. (1961) Biochem. Pharmacol. 7:88-95. Abstract Only.*

\* cited by examiner

*Primary Examiner*—Lisa J Hobbs
(74) *Attorney, Agent, or Firm*—Birch, Stewart, Kolasch & Birch, LLP

(57) ABSTRACT

The present invention relates to a bioassay element and its producing method. The bioassay element includes a carrier, a testing material, and a coating film, in which the testing material is dispersed in the coating film which covers on the surface of the carrier and comprises a casein and calcium ions. The bioassay element is produced by applying a bioassay solution which includes a testing material, a casein and calcium ions to the carrier, and then drying the bioassay solution.

8 Claims, 6 Drawing Sheets

METHOD FOR PRODUCING ACTIVE AND STABLE ACETYLCHOLINESTERASE BIOASSAY ELEMENT

FIELD OF THE INVENTION

The present invention relates to a bioassay element and its producing method.

BACKGROUND OF THE INVENTION

In order to solve a problem associated with pesticide residues that are contained in commercial vegetables and fruits, it is necessary to develop a method to screen pesticide residues rapidly and thus to invent a disposable, cheap bioassay kit, which can be used to detect pesticide residues immediately. Till recently, the major pesticides widely used in agricultural fields are organic phosphorus compounds and carbarmates; these pesticides can be detected by using a bioassay kit which is sensitive to the pesticides.

Enzyme immobilization is a critical technique for the development of a bioassay kit. Compared with immobilized enzymes in a "solution" state, immobilized enzymes in a "dry" state can reduce the decreasing rate of enzyme activity. This is highly advantageous to extend the preservative time of the bioassay kit. However, after the enzyme is immobilized and adsorbed onto the surface of a carrier, the activity of the enzyme declines to approximately one tenth of total activity of the original enzyme. Regarding the pesticides-detecting bioassay kits, the enzyme-immobilized carrier plays an influential role in the calorimetric process of pesticide residues screening when the Ellman test is used. The examination for color change on the enzyme-immobilized carrier by human eyes will provide a simple indication of enzyme inhibition or being free of inhibition due to the presence of pesticides or not. Once the enzyme-immobilized carrier is dipped into the aqueous substrate solution, elution of the enzyme or/and colorimetric products may occur, resulting in the reduction of detection sensitivity of the chromaticity by human eyes. There are a variety of methods for the immobilization of the enzyme, including physical adsorption, ion binding, covalent binding, cross-linking, entrapments, etc. According to U.S. Pat. No. 5,624,831, gelatin and trehalose can be used to form a stable film through a synergistic effect of these two materials and then an enzyme can be successfully entrapped into the stable film. The enzyme can maintain its activity at 100% and can be preserved up to 31 days under a dry condition and in a temperature of 4° C., room temperature, or even 50° C. Nevertheless, the enzyme immobilized by this method may reduce its activity to 70% after preserving 31 days under a dry condition and in temperature of 37° C.

SUMMARY OF THE INVENTION

The main objective of the present invention is to provide a bioassay element and its producing method by which a cheap bioassay kit that may maintain the activity of a testing material for a long time can be established.

The bioassay element according to the present invention includes a carrier, a testing material, and a coating film. The testing material disperses in the coating membrane, and the coating film that covers on the surface of the carrier consists of casein and calcium ions. The coating membrane can not only effectively increase the immobilized amount of the testing material, but also raise the activity of the testing material. The testing material can be restricted at the surface of the carrier.

DETAILED DESCRIPTION OF THE INVENTION

In the bioassay element of the present invention, the carrier includes a membrane and a stationary layer applying to the membrane, and a testing material is dispersed in the coating film and the coating film covers the surface of the stationary layer. The stationary layer consists of casein and calcium ions, which can function as an adhesive to attach both the coating film and the membrane.

The coating film and the stationary layer may use casein as a main constituting material due to its low cost. Unlike the other proteins with a stable three-dimensional structure, the casein has an irregularly flexible structure, and hence it has different chemical properties, compared with the other proteins; for example, it possesses a heat resistance, a low interfacial free energy, a high viscosity, and so on. Particularly, an increase of the concentration of calcium ions ($Ca^{2+}$) may remarkably affect a parameter of interfacial viscosity of casein. When the concentration of calcium ions reaches to the threshold of 12 mM or higher, casein and the calcium ions can bind to form a gel-like protein structure that results in an increase of the viscosity.

The present invention further includes a method of producing the bioassay element, which comprises steps of providing a carrier; applying a bioassay solution which contains a testing material, casein and calcium ions to the carrier; and drying the bioassay solution.

The present invention is illustrated more detailed as follows by referring to the accompanying drawings.

Figure 1:
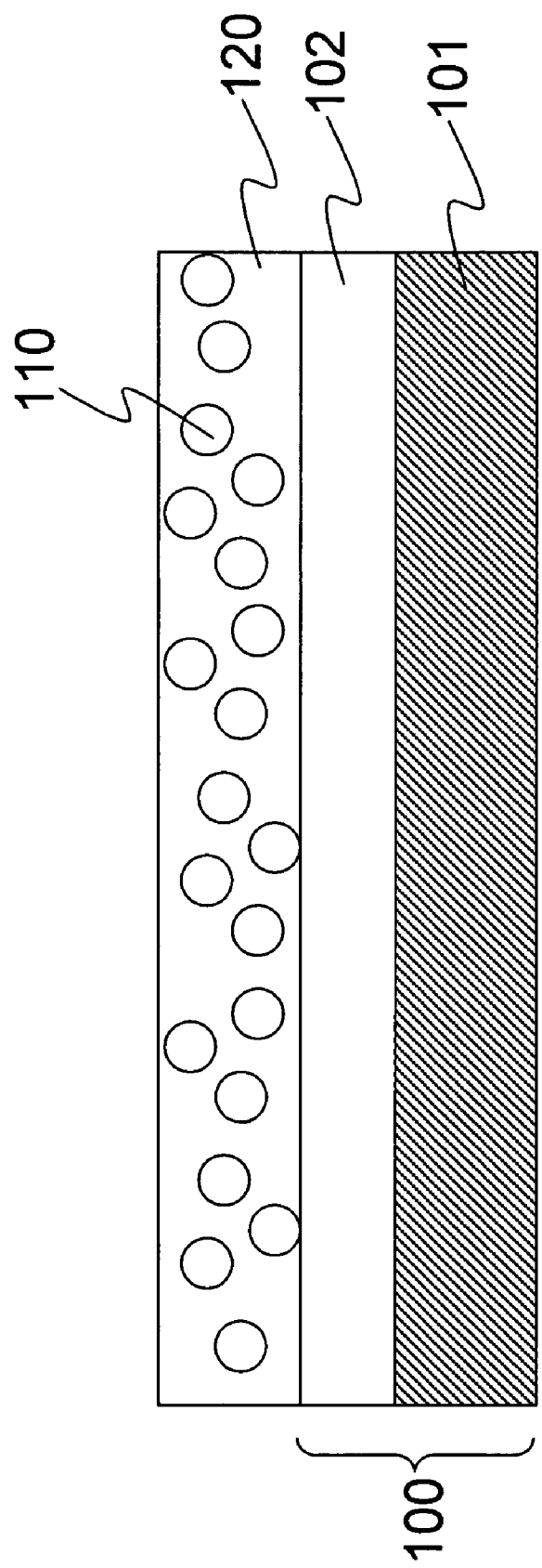
FIG. 1 illustrates a structure of the bioassay element of one embodiment of the present invention.

The bioassay element of the present invention is referred to FIG. 1 which illustrates the structure of bioassay element in one embodiment of the present invention. The bioassay element includes a carrier 100, an enzyme 110 as a testing material, and a coating film 120. The carrier includes a membrane 101 and a stationary layer 102 applying on the membrane 101. The enzyme 110 is dispersed in the coating film 120 that covers on the surface of the stationary layer 102. The coating film 120 effectively increases the amount of the immobilized enzyme 110 and raises the activity of the enzyme 110 and fixes the enzyme 110 on the surface of the carrier. In the working example of the present invention, the enzyme acetylcholinesterase is selected, and the coating film 120 consists of casein, calcium ions, a color developer (DTNB), and trehalose. The stationary layer 102 consists of casein and calcium ions.

Figure 2:
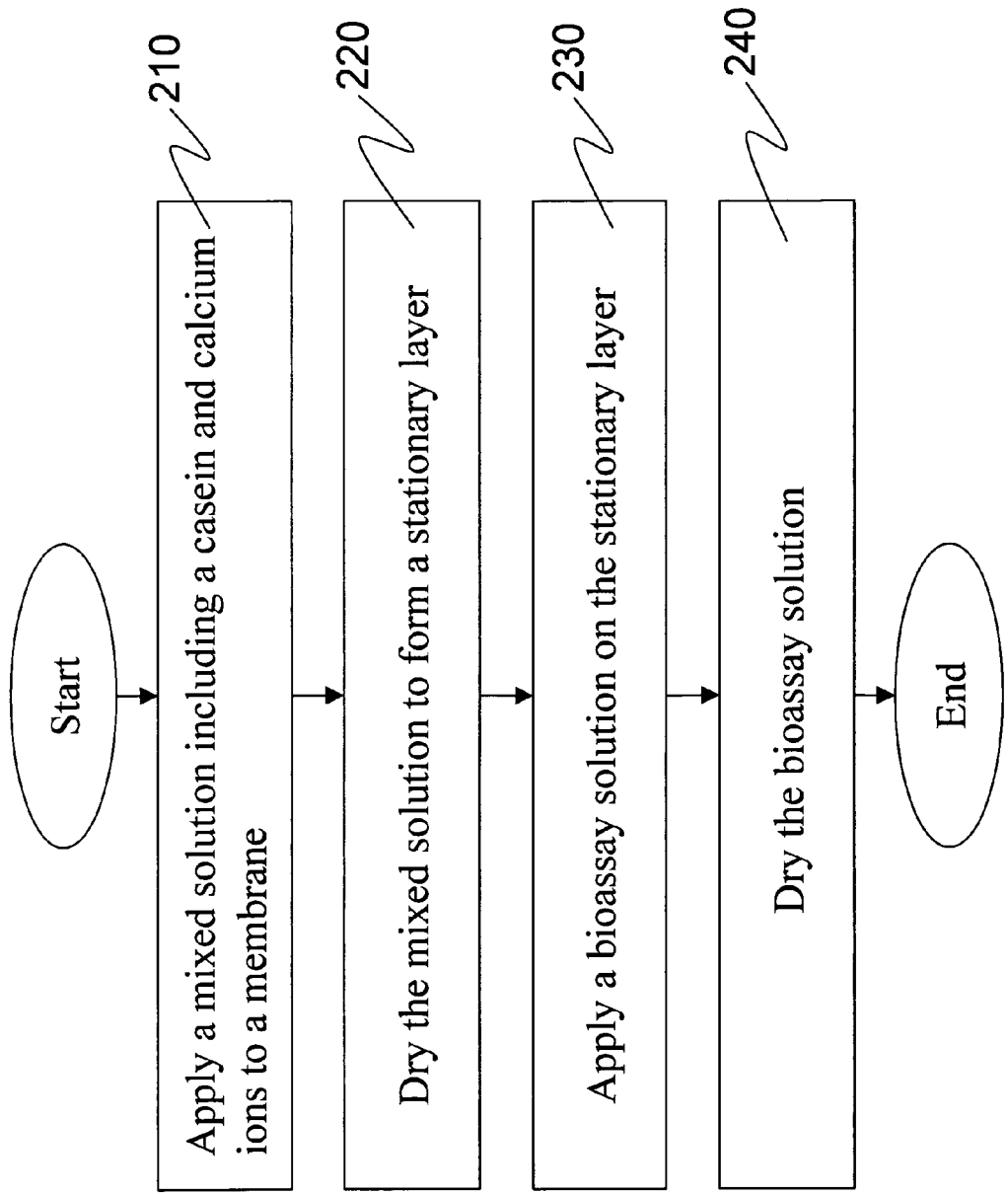
FIG. 2 is a flow chart illustrating a process for preparing the bioassay element of one embodiment of the present invention.

A flow chart illustrating the method for producing the bioassay element of the embodiment of the present invention is referred to FIG. 2. The method comprises the steps of applying a mixed solution which includes casein and calcium ions to a membrane (Step 210); drying the mixed solution to form a stationary layer (Step 220); applying a bioassay solution which includes an enzyme as a testing material, casein, calcium ions, a color developer (DTNB), and trehalose to a carrier (Step 230); and drying the bioassay solution (Step 240). The procedures of drying could be air dried, vacuum dried, or suction dried.

In the working example of the present invention, the stationary-layer mixed solution was prepared by mixing 120 mM of a calcium ion solution and 2.5% of a casein solution in a ratio of 1:14 by volume. The bioassay solution was prepared by mixing an enzyme solution and the mixed solution containing casein in a ratio of 5:7 by volume. The enzyme solution was prepared by mixing 1.52 U/µl of an enzyme and 5% of trehalose in a ratio of 2.61:108 by volume. The mixed solution containing casein was mixed with a color developer, 120 mM of a calcium ion solution and 4% of a casein solution in a ratio of (0.009 to 0.012):1:(6 to 7.75) (w/v/v).

Figure 3:
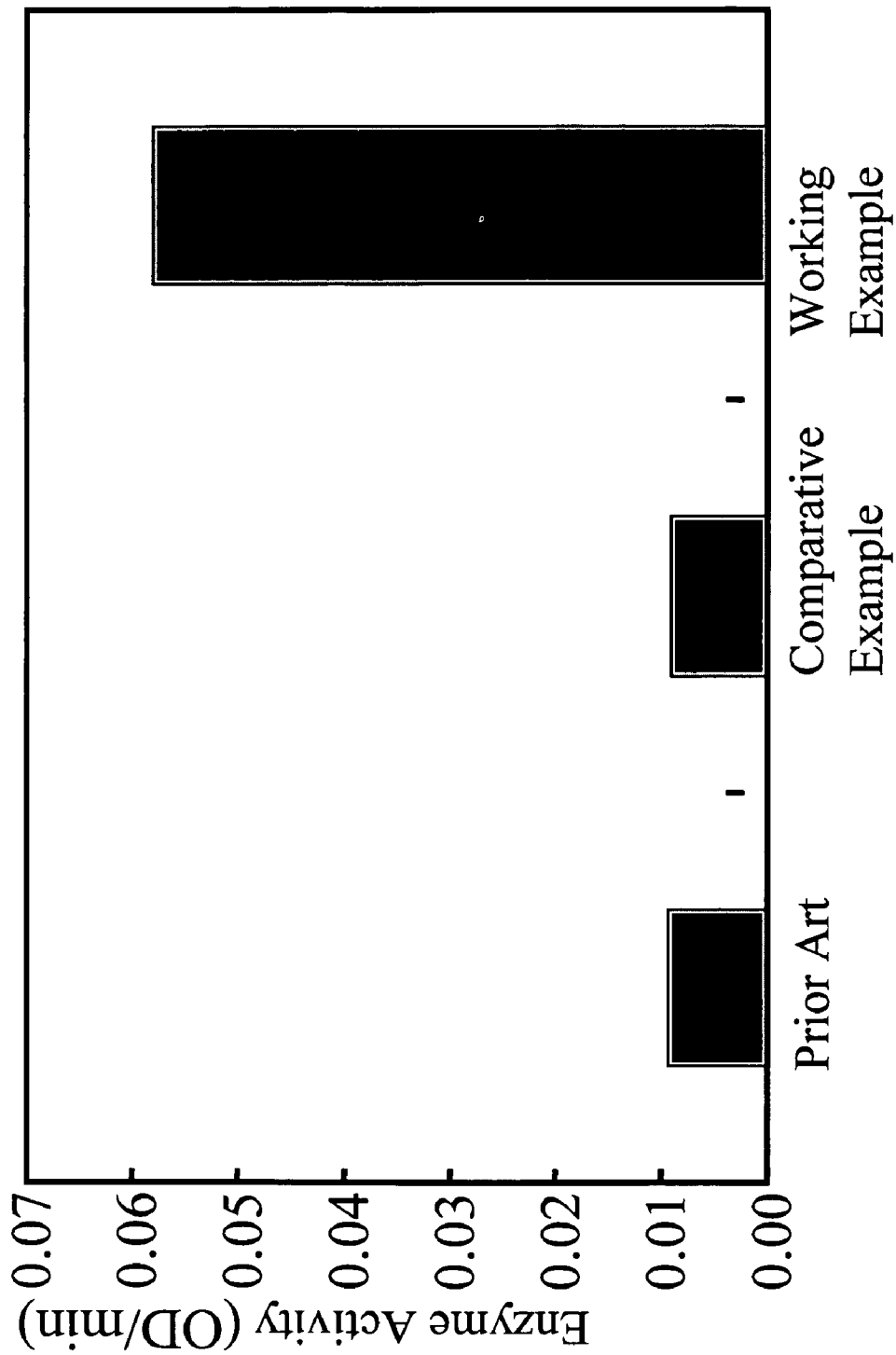
FIG. 3 shows enzyme activity in the bioassay elements of a prior art, a comparative example, and a working example of the present invention.

The bioassay element produced in the working example of the present invention, the bioassay element of prior art that used gelatin to disperse an enzyme, and the bioassay element (comparative example) that produced under the same conditions as the working example of the present invention but without adding calcium ions were individually measured for their enzyme activity. The results of enzyme activity are referred to FIG. 3. Compared with the prior art and the comparative example, the enzyme activity in the bioassay element of the working example of the present invention increased about six folds. Obviously, the addition of calcium ions ($Ca^{2+}$) had a great effect on the activity of the immobilized enzyme.

Figure 4:
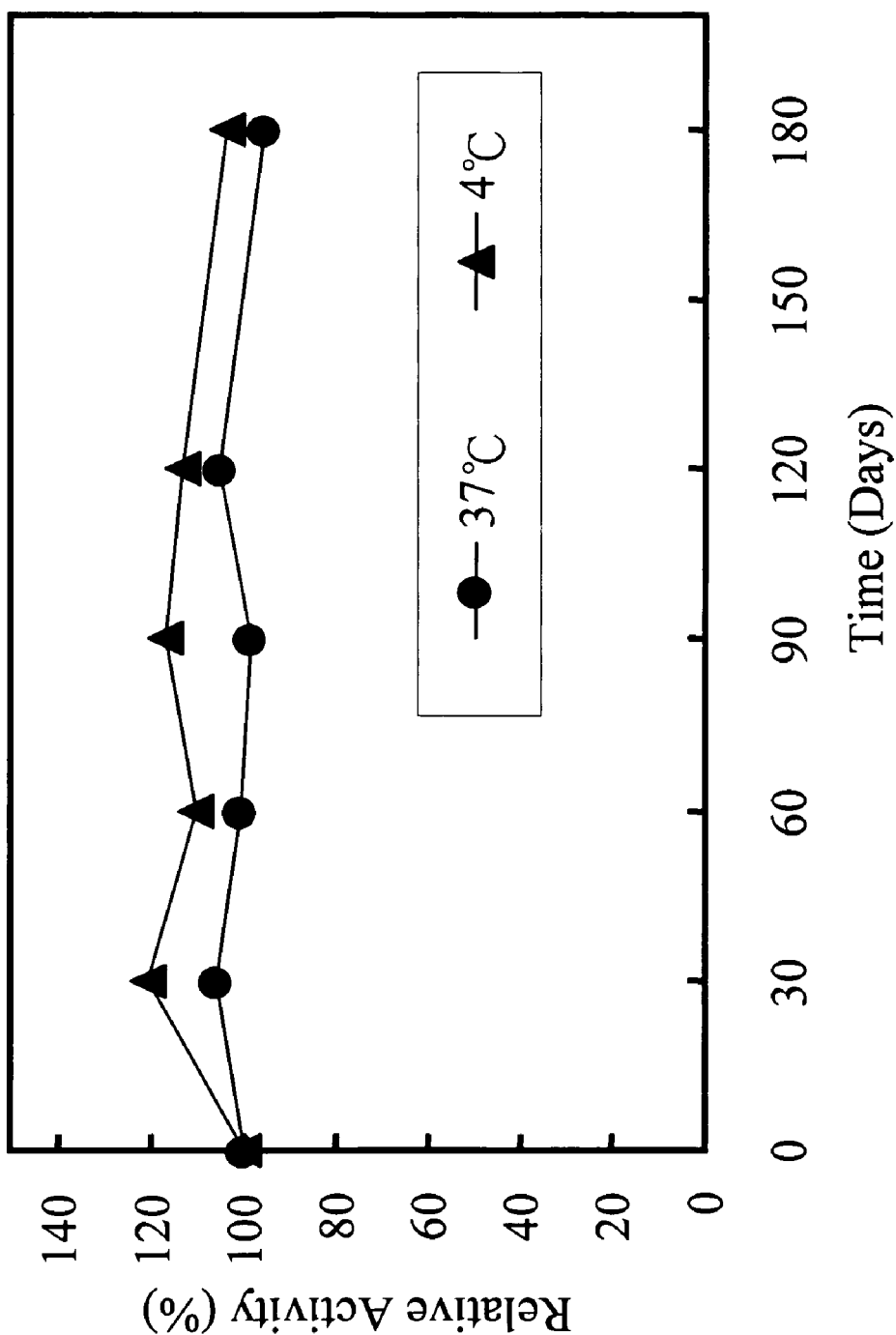
FIG. 4 shows enzyme activity of the bioassay element produced in the working example of the present invention.

Moreover, when the bioassay element of the present invention was preserved under the temperature of 37° C. and 4° C. for 180 days, the enzyme activity was measured for every 30 days. The results of the enzyme activity of bioassay element of the working example of the present invention are referred to FIG. 4. The results showed that the bioassay element maintained 80% to 120% activity of the enzyme after being preserved for 90 days. After being preserved for 180 days under the temperature of either 37° C. or 4° C., the bioassay element still maintained the enzyme activity at 100%.

Figure 5:
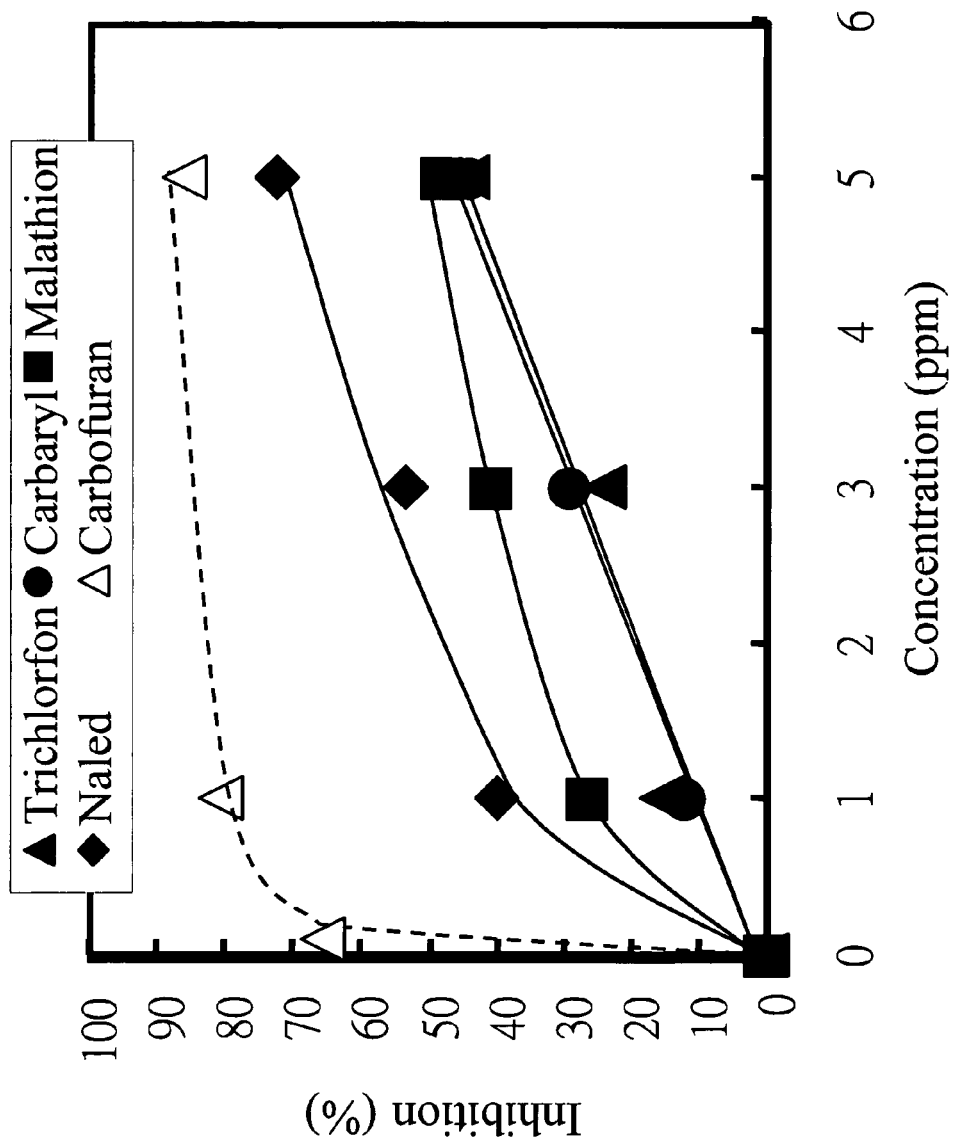
FIG. 5 shows inhibition of the bioassay element produced in the working example of the present invention against several pesticides at different concentrations.

The results of the inhibiting effect of several pesticides (with different concentrations) on the bioassay element of the present invention are referred to FIG. 5. The results showed that the inhibition of the enzyme activity against the pesticides increased with increasing concentrations of trichlorfon and carbaryl. Regarding malathion and naled at a concentration in a range of 0 to 1 ppm, it exhibited a linear relationship between the pesticides concentration and the inhibition of the enzyme activity, and the increase of the inhibition is plateau when the pesticides concentration was greater than 1 ppm. Concerning carbofuran at a concentration in a range of 0 to 0.1 ppm, it exhibited a linear relationship between the pesticide concentration and the inhibition of the enzyme activity, the increase of inhibition is plateau when the carbofuran concentration was greater than 0.1 ppm. Meanwhile, in the case of any concentration of the pesticides, the inhibiting effect of the pesticides on the enzyme activity exhibited in the following decreasing order: carbofuran>naled>malathion>carbaryl=trichlorfon. At the same concentration, the higher inhibition represents that the enzyme has higher detection sensitivity to pesticide. Consequently, for these five pesticides, the bioassay element showed that the detection sensitivity for carbofuran was the highest, naled and malathion were the next, and carbaryl and trichlorfon were the lowest. Within the linear relationship between the concentration of each pesticide and the inhibition of the enzyme, a biosensor capable of quantitatively detecting pesticides in association with optical sensors can be designed.

Figure 6:
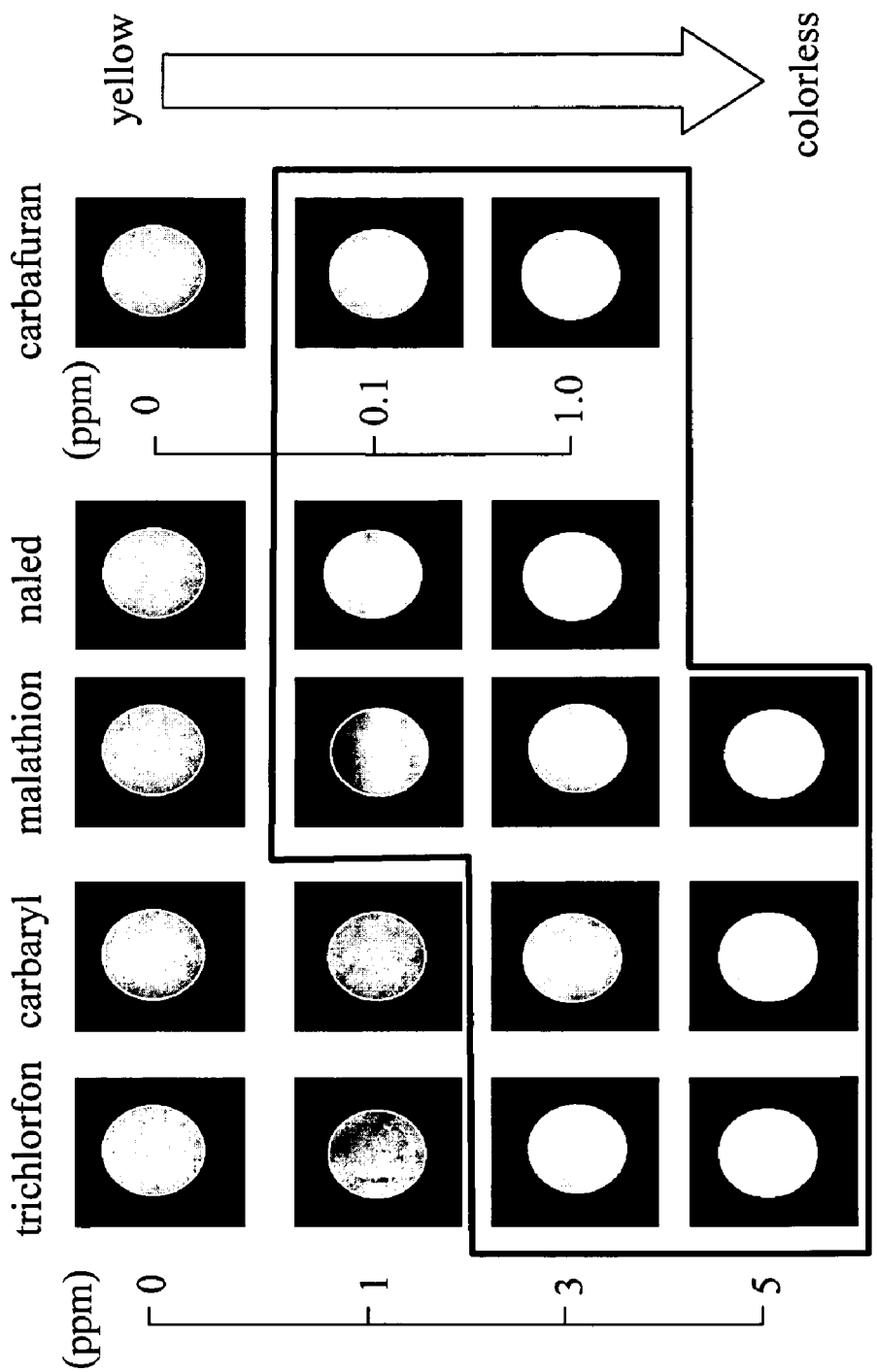
FIG. 6 shows color of the bioassay element produced in the working example of the present invention against several pesticides at different concentrations.

As shown in FIG. 6, the results showed that the color would change from yellow to yellowish when the inhibition of the enzyme activity increased. If the inhibition of the enzyme activity is greater than 60%, the color will become colorless. To discriminate the color change by human eyes, the concentrations of trichlorfon and carbaryl are about 3 ppm, malathion and naled are about 1 ppm, carbafuran is about 0.1 ppm.

Using the data of FIG. 5, when the concentrations of trichlorfon and carbaryl were 3 ppm, the inhibition of the enzyme activity was about 28%. When the concentrations of malathion and naled were 1 ppm, the inhibition of the enzyme activity were 28% and 39%, respectively. When the concentration of carbafuran was about 0.1 ppm, the inhibition of the enzyme activity was 65%. Therefore, if the inhibition of the enzyme activity is greater than 30%, it should be very easy to distinguish the yellow-color level difference by human eyes. In addition, when the concentration of naled was greater than 3.5 ppm and the concentrations of malathion, trichlorfon and carbaryl were greater than 7 ppm, the inhibition of the enzyme activity would be greater than 60%. Thus, the color would become colorless. Hence, these data are helpful for adjusting the parameter of bioassay element producing.

Although the present invention is exemplified by the above preferable working example, it is not to restrict the scope of the present invention. Person skilled in the art can make a certain modification and change without departing from the sprit and scope of the present invention. Therefore, it is necessary to define the scope of the present invention based on the claims described below.

What is claimed is:

1. A method of producing a bioassay element, which comprises steps of:
measuring initial enzyme activity of acetylcholinesterase;
providing a membrane;
applying a bioassay solution which includes said acetylcholinesterase, casein and calcium ions to said membrane, wherein the weight ratio of said casein and said calcium ions is 1:2.688;
drying said bioassay solution; and
storing said bioassay element at 37° C. or lower, wherein said acetylcholinesterase maintains at least 80% of said initial activity after being preserved for 90 days.

2. A method of producing a bioassay element, which comprises steps of:
measuring initial enzyme activity of acetylcholinesterase;
providing a membrane;
applying a solution which includes casein and calcium ions on the membrane, wherein the weight ratio of said casein and said calcium ions is 1:2.688;
drying said solution to form a stationary layer on said membrane;
applying a bioassay solution which includes said acetylcholinesterase, casein and calcium ions on the stationary layer, wherein the weight ratio of said casein and said calcium ions is 1:2.688;
drying said bioassay solution; and
storing said bioassay element at 37° C. or lower, wherein said acetylcholinesterase maintains at least 80% of said initial activity after being preserved for 90 days.

3. A method according to claim 2, wherein said solution that forms said stationary layer is dried by means of air drying, vacuum drying, suction drying, or a combination thereof.

4. A method according to claim 2, wherein said solution that forms said stationary layer is prepared by mixing 120 mM of a calcium ion solution and 2.5% of a casein solution in a ratio of 1:14 by volume.

5. A method according to claim 1, wherein said bioassay solution is dried by means of air drying, vacuum drying, suction drying, or a combination thereof.

6. A method according to claim 2, wherein said bioassay solution is dried by means of air drying, vacuum drying, suction drying, or a combination thereof.

7. A method according to claim 1, wherein said acetylcholinesterase maintains at least 80% of said initial activity after being preserved for 180 days.

8. A method according to claim 2, wherein said acetylcholinesterase maintains at least 80% of said initial activity after being preserved for 180 days.

* * * * *